(12) United States Patent
Gabbay (10) Patent No.: US 7,025,780 B2
(45) Date of Patent: Apr. 11, 2006

(54) VALVULAR PROSTHESIS

(76) Inventor: Shlomo Gabbay, #1 Randall Dr., Short Hills, NJ (US) 07078

( * ) Notice: Subject to any disclaimer, the term of this patent is extended or adjusted under 35 U.S.C. 154(b) by 213 days.

(21) Appl. No.: 10/373,138

(22) Filed: Feb. 24, 2003

(65) Prior Publication Data
US 2003/0149477 A1 Aug. 7, 2003

Related U.S. Application Data

(63) Continuation of application No. 09/659,882, filed on Sep. 12, 2000, now abandoned.

(51) Int. Cl.
*A61F 2/24* (2006.01)
(52) U.S. Cl. ............ 623/2.13; 623/2.17; 623/900
(58) Field of Classification Search .......... 623/1.24, 623/1.26, 2.14, 2.15, 2.16, 2.17, 2.18, 2.19, 623/900
See application file for complete search history.

(56) References Cited

U.S. PATENT DOCUMENTS

| 5,855,597 A | 1/1999 | Jayaraman ............. 623/1.16 |
| 5,855,601 A * | 1/1999 | Bessler et al. ............ 623/900 |
| 5,935,163 A * | 8/1999 | Gabbay ................. 623/2.14 |
| 6,425,916 B1 * | 7/2002 | Garrison et al. ........ 623/1.26 |
| 2001/0020181 A1 | 9/2001 | Layne |
| 2001/0021872 A1 | 9/2001 | Bailey et al. |

OTHER PUBLICATIONS

Ross D., Pulmonary valve autotransplantation (the Ross operation), Sep. 1988, J. Cardiac Surgery, 3:313-9.*

* cited by examiner

*Primary Examiner*—Brian E. Pellegrino
(74) *Attorney, Agent, or Firm*—Tarolli, Sundheim, Covell & Tummino L.L.P.

(57) ABSTRACT

A valvular prosthesis and method of using the prosthesis are disclosed. A valve apparatus is located within a stent apparatus, such that the prosthesis is deformable between a first condition and a second condition, in which the prosthesis has a reduced cross-sectional dimension relative to the first condition, whereby implantation of the prosthesis is facilitated when in the second condition.

6 Claims, 5 Drawing Sheets

VALVULAR PROSTHESIS

RELATED APPLICATION

This application is a continuation of U.S. patent application Ser. No. 09/659,882, which was filed on Sep. 12, 2000, now abandoned and entitled VALVULAR PROSTHESIS AND METHOD OF USING SAME, which is incorporated herein by reference.

TECHNICAL FIELD

The present invention relates to an implantable prosthetic device and, more particularly, to a valvular prosthesis and to a method of using the prosthesis.

BACKGROUND

It is well known to utilize mechanical heart valves, such as the ball check valve, and natural tissue cardiac valves to replace defective aortic and mitral valves in human patients. One type of natural tissue heart valve typically employs a porcine valve for implantation in a human, as they are very similar to human valves of appropriate size and generally are easy to procure. Typically, the porcine valve is fixed by chemically treating it, such as with an appropriate glutaraldehyde solution. The treated porcine valve further may be mounted into a stent to support the valve at a fixed position.

A stent typically is formed of a resilient material, such as a plastic (e.g., DELRIN). Examples of various stent structures are disclosed in U.S. Pat. No. 3,983,581, U.S. Pat. No. 4,035,849. The stent usually is covered with a fabric material, such as DACRON or a suitable textile material. The fabric material provides structure for securing the valve relative to the stent. The stented heart valve prosthesis may be implanted into a patient for a heart valve replacement.

In order to surgically implant a heart valve into a patient, the patient typically is placed on cardiopulmonary bypass during a complicated, but common, open chest procedure. In certain situations, an individual requiring a heart valve replacement may be sufficiently ill, such that placing the individual on cardiopulmonary bypass may pose too great a risk. Such individuals may correspond to a class of patients who may have a non-functioning pulmonary valve or severe aortic valve insufficiency. In particular, older patients having a deficient aortic valve may be too ill to survive conventional open-heart surgery.

Another class of individuals may be suffering from vascular degeneration associated with the lower extremities. Such degeneration may include inoperative or otherwise ineffective venous valves resulting in one or more undesirable indications.

These and other conditions would benefit from an improved valvular prosthesis that may be implanted by a less invasive and/or less time-consuming implantation procedure.

SUMMARY

The present invention relates to a valvular prosthesis operable to mitigate valvular insufficiency. The prosthesis includes a valve apparatus located within a stent apparatus to form a stented valve. The stented valve is deformable between reduced and expanded cross-sectional dimensions. For example, the stented valve may be deformed to the reduced cross-sectional dimension to facilitate positioning the stented valve to a desired implantation position. The valve can then be permitted to expand from the reduced cross-sectional dimension to the expanded cross-sectional dimension such as to replace an insufficient heart valve or an insufficient venous valve.

In accordance with one aspect, the stented valve may be deformed to the reduced cross-sectional dimension by placement within a retaining mechanism, such as a generally cylindrical enclosure of a catheter apparatus. The enclosure may be employed to position the stented valve at a desired position and then discharge the prosthesis from the enclosure. The stented valve then expands toward the expanded cross-sectional dimension and at least a portion of the outer surface of the stent engages surrounding tissue to inhibit axial movement of the stented valve relative to the surrounding tissue.

BRIEF DESCRIPTION OF THE DRAWINGS

To the accomplishment of the foregoing and related ends, certain illustrative aspects of the invention are described herein in connection with the following description and the annexed drawings. These aspects are indicative, however, of but a few of the various ways in which the principles of the invention may be employed and the present invention is intended to include all such aspects and their equivalents. Other advantages and novel features of the invention will become apparent from the following detailed description of the invention when considered in conjunction with the drawings, in which.

DESCRIPTION OF THE INVENTION

Figure 1:
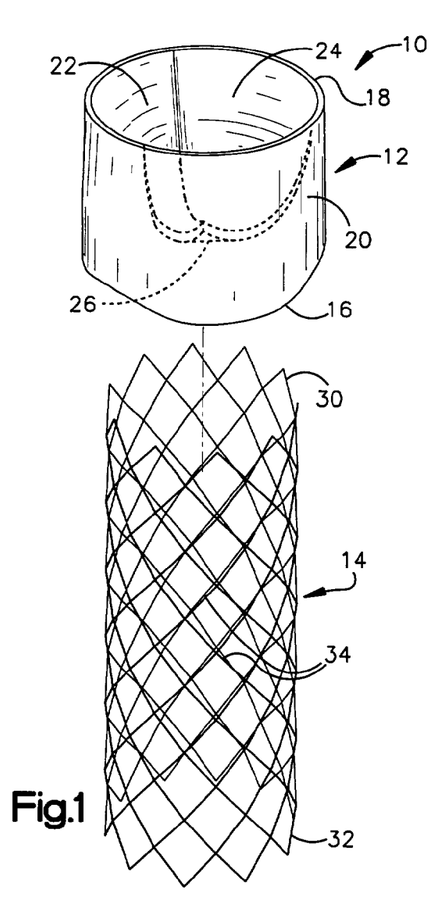
FIG. 1 is an exploded isometric view of a valve and stent apparatus that may be utilized to form a prosthesis in accordance with the present invention.
Figure 2:
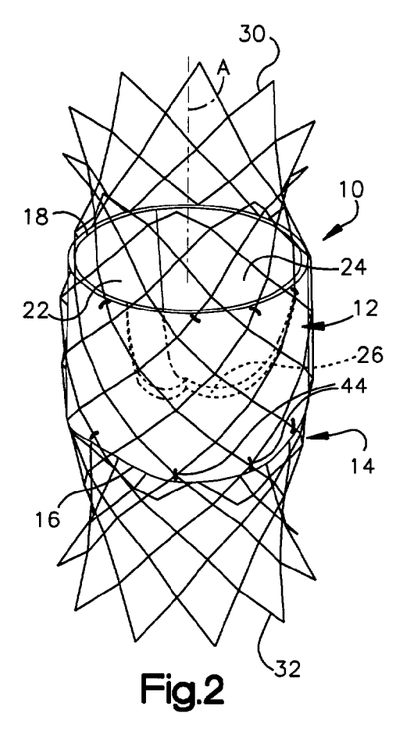
FIG. 2 is an example of a valvular prosthesis in accordance with the present invention.

FIG. 1 is an exploded view of a valvular prosthesis 10 in accordance with an aspect of the present invention. The prosthesis 10 includes a valve portion 12 and a stent portion 14 that may be assembled to form the valvular prosthesis 10, such as shown in FIG. 2.

The valve portion 12 includes inflow and outflow ends 16 and 18 spaced apart from each other by a length of a generally cylindrical sidewall portion 20. While the inflow and outflow ends 16 and 18 are illustrated as being annular in FIGS. 1 and 2, those skilled in the art will understand and appreciate that other configurations (e.g., generally sinusoidal ends) also could be used in accordance with the present invention.

The valve portion 12 also includes one or more leaflets 22, 24, and 26 that are attached to and extend from an interior of the sidewall portion 20. In the example illustrated in FIGS. 1 and 2, the valve portion 12 includes three leaflets 22, 24 and 26, although other numbers of leaflets, such as a single leaflet or two leaflets, also could be used.

The valve portion 12 may be formed of any substantially biocompatible valve apparatus. By way of example, the valve portion 12 may include an animal heart valve (e.g., pulmonic or aortic), a manufactured valve device (e.g., a valve as shown and described in U.S. Pat. No. 4,759,758 or U.S. Pat. No. 5,935,163) a venous valve (e.g., a bovine or equine jugular venous valve). Those skilled in the art will understand and appreciate that the foregoing list is not intended to be exhaustive but, instead, is intended illustrate a few examples of the types of valves that may be utilized in a valvular prosthesis 10 in accordance with an aspect of the present invention.

If the valve portion 12 is formed of a natural tissue material, such as an animal heart valve, a venous valve, or a composite valve manufactured of natural tissue, the valve should be chemically fixed, such as in a suitable solution of glutaraldehyde in a closed condition (as is known in the art). The fixation process facilitates closure of the valve 12 under application of back flow pressure, while remaining open during normal forward blood flow through the valve 12. By way of example, the natural tissue valve may be cross-linked with glutaraldehyde and undergo a detoxification process with heparin bonding, such as according to a NO-REACT® treatment process from Shelhigh, Inc. of Millburn, N.J. The NO-REACT® treatment improves biocompatibility of the valve apparatus 12 and mitigates calcification and thrombus formation.

In accordance with an aspect of the present invention, the valve portion 12 exhibits structural memory. That is, if the valve apparatus 12 is compressed, such as to a reduced diameter at the time of being implanted, it will return substantially to its original shape and configuration upon removal of radially inward forces. As a result, the valve apparatus 12 is able to maintain coaptation of the leaflets 22, 24, and 26 even after being deformed. The memory feature of the valve is further improved by mounting it within the stent portion 14.

Turning now to the stent portion 14, such as shown in FIGS. 1 and 2, the stent includes an inflow end 30 and an outflow end 32. In this example, the inflow and outflow ends 30 and 32 are spaced apart from each other a distance that is greater than the distance between the corresponding ends 18 and 16 of the valve 12. In this way, the ends of the stent 30 and 32 may extend beyond the respective ends 18 and 16 of the valve 12 (e.g., by about a few millimeters), such as shown in FIG. 2. The stent portion 14 also may include outwardly turned portions at the inflow and outflow ends 30 and 32 of the stent, which, when implanted, may engage and/or be urged into the surrounding tissue to mitigate movement thereof.

According to an aspect of the present invention, the stent 14 may deformable between first and second conditions, in which the first condition has a reduced cross-sectional dimension relative to the second condition. FIGS. 1 and 2 illustrate the stent portion 14 as being formed of a mesh or weave 34 extending between the ends 30 and 32. The mesh 34 may be a metal, an alloy, or other suitable material that may help support a valve mounted therein and/or help anchor the valve at a desired position when implanted.

By way of example, the mesh may be formed of a shape memory alloy material, such as may be formed of a nitinol (nickel-titanium alloy) wire. Shape memory (or thermal memory) is a characteristic in which a deformed part remembers and recovers to a pre-deformed shape upon heating. By forming the stent 14 of a shape memory alloy, the stent is inelastically deformable to new shape, such as a reduced cross-sectional dimension, when in its low-temperature (martensitic) form. For example, the stented valve (FIG. 2) may be cooled, such as by being introduced to a cooling solution (e.g., water), and then compressed.

When the stent 14 is heated to its transformation temperature, which may vary according to the alloy composition, it quickly reverts to its high-temperature (austenitic) form. The stented valve may retain the compressed condition by keeping it cooled. Alternatively, the stent and valve may be retained in the compressed position, such as with sutures circumscribing the structure, a cylindrical enclosure around the structure, etc. The prosthesis 10 will then return toward its high-temperature (or original) position upon removal of the retaining element.

It is to be appreciated that, alternatively, the stent 14, in accordance with an aspect of the present invention, could be inelastically deformable so as to require an intervening force to return the deformed stent substantially to a desired configuration. For example, a balloon catheter or spring mechanism could be employed to urge the stent and the valve located therein generally radially outward so that, after being implanted to a desired position, the stent will engage the surrounding tissue in a manner to inhibit movement relative to the surrounding tissue.

Figure 1A:
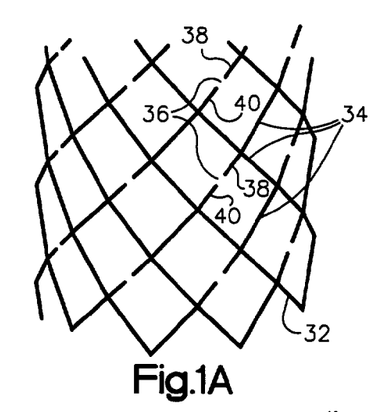
FIG. 1A in enlarged view of part of the stent of FIG. 1 in a first condition.
Figure 1B:
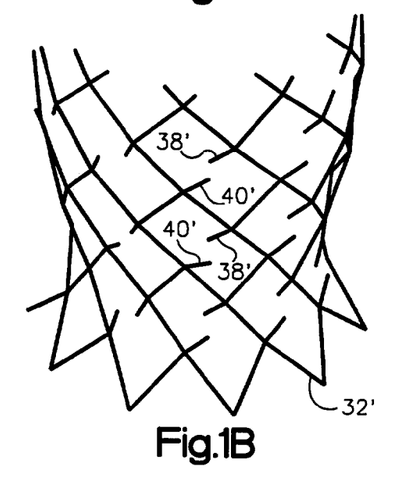
FIG. 1B is enlarged view of part of the stent of FIG. 1, similar to FIG. 1A, illustrating the part of the stent in a second condition.

FIGS. 1A and 1B illustrate an enlarged view of part of the stent 14 in accordance with an aspect of the present invention. In this example, some strands of the mesh 34 are broken to define spaces 36 between adjacent lateral extensions or spike portions 38 and 40. As the stent 14 is deformed, such as shown in FIG. 1B, the spike portions 38' and 40' may extend radially outwardly from the stent in different directions. In addition, the inflow end 32' also may flare outwardly for engagement with surrounding tissue when implanted. For example, some spikes 40, 40' may extend generally outwardly and toward an outflow end of the stent 14, while others 38, 38' may extend generally outwardly and toward an inflow end 32, 32'. The spikes thus are operable to engage tissue, when implanted, so as to inhibit axial movement of the stent 14 relative to the surrounding tissue.

Referring back to FIG. 2, the valve portion 12 is disposed generally coaxially within the cylindrical stent portion 14 relative to the central axis A. The valve 12 may be affixed relative to the stent portion 14, such as by one or more sutures 44. The sutures 44 may be located at the inflow and outflow ends 16 and 18 of the valve 12 to connect the valve to the stent 14 to inhibit axial movement of the valve relative to the stent. Alternatively or additionally, axial movement between the stent 14 and valve 12 may be mitigated due to friction fitting between the stent and valve portion. For example, as illustrated in FIG. 2, the valve portion 12 has a cross-sectional diameter that is slightly larger than that of the stent 14, such that the prosthesis 10 bulges somewhat in the middle and is narrower near the inflow and outflows ends 16 and 18 of the valve portion 12.

As mentioned above, the stent portion 14 may be formed of a shape memory alloy. In this way, the valvular prosthesis 10 may be compressed to a reduced cross-sectional dimension about the axis A and maintained at the reduced dimension while being implanted. Once the valvular prosthesis 10 is at a desired implantation position, the prosthesis may be permitted to return toward its original cross-sectional dimension so as to engage a valve wall or other surrounding tissue at the desired position. The engagement between the stented valvular prosthesis 10 and the surrounding tissue inhibits axial movement of the prosthesis relative to the tissue. In accordance with an aspect of the present invention, lateral extensions or spikes (see, e.g., FIGS. 1A and 1B) may extend outwardly from the stent to further inhibit axial movement. Those skilled in the art will understand and appreciate that a valvular prosthesis 10, in accordance with the present invention, may be utilized to replace a heart valve or utilized as an intravascular implant to provide an operable venous valve.

Figure 3:
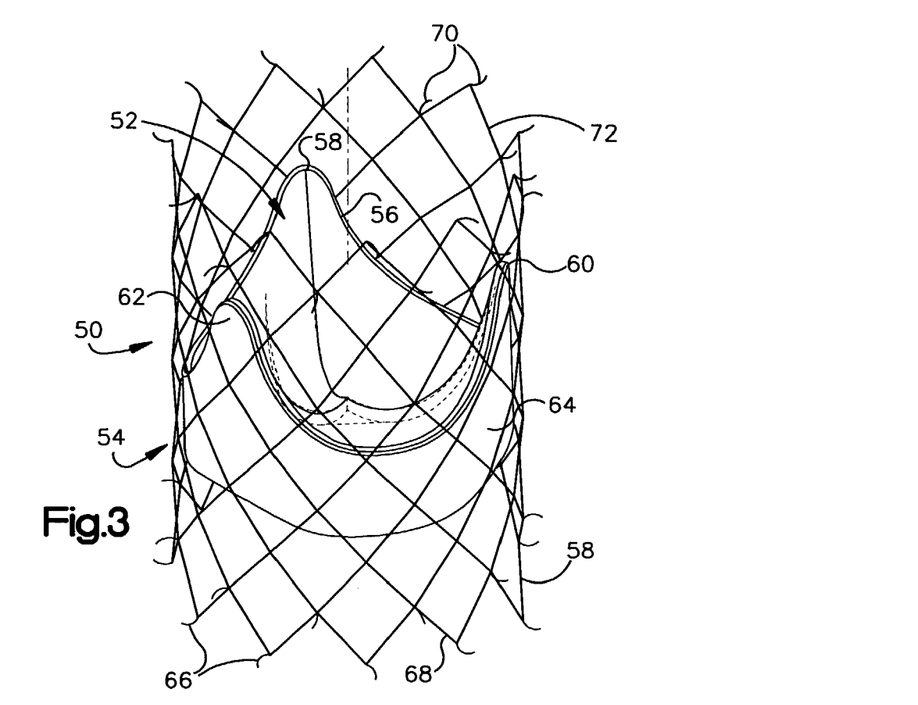
FIG. 3 is another example of valvular prostheses in accordance with the present invention.

FIG. 3 illustrates another example of a stented valvular prosthesis 50 in accordance with an aspect of the present invention. The prosthesis 50 in this example includes a valve portion 52 mounted within a stent portion 54. The valve portion 52 in this example, has a generally sinusoidal outflow end 56 having a plurality of commissure posts 58, 60, and 62 extending from an annular base portion 64, with corresponding sinuses located between each adjacent pair of posts. It is to be appreciated that, alternatively, a valve having a sidewall portion according to generally cylindrical configuration of FIGS. 1 and 2 also could be used in conjunction with the stent portion 54.

The stent portion 54 in this example is formed of a deformable mesh, which may be substantially identical to that described above with respect to FIGS. 1–2. The stent portion 54 also includes a plurality of spikes extending generally radially outwardly from the stent portion. In particular, one set of spikes 66 extend from an inflow end 68 of the stent portion 54 and another set of spikes 70 extend from an outflow end 72 of the stent.

Figure 4:
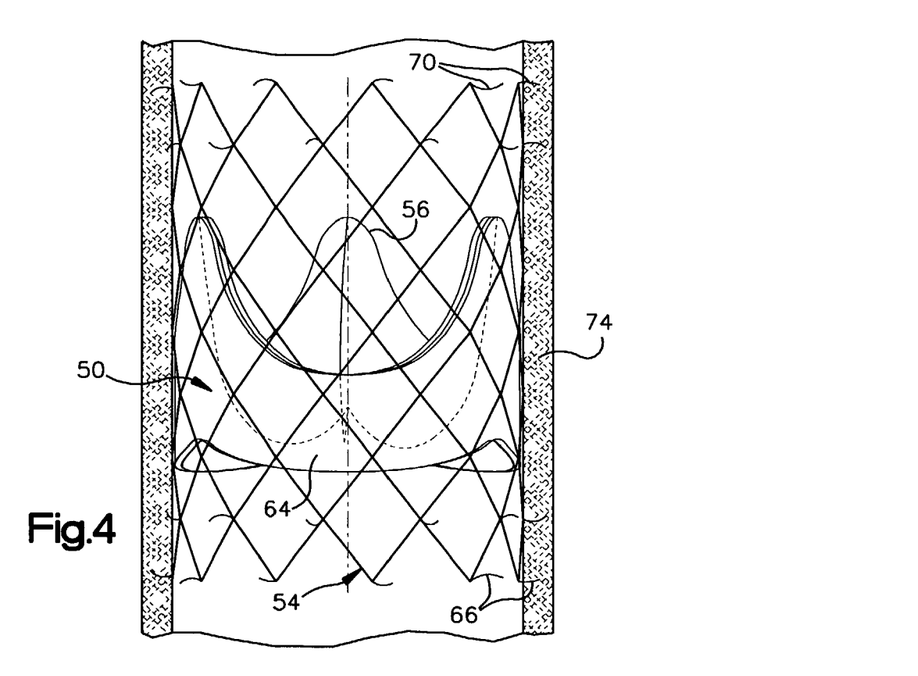
FIG. 4 is an example of the valvular prostheses of FIG. 3 implanted within a tubular member in accordance with the present invention.

FIG. 4 illustrates the prosthesis 50 of FIG. 3 mounted in an expanded condition within a generally cylindrical sidewall 74. The sidewall 74, for example, may be a venous valve wall, a pulmonary artery, an aorta, etc. In this example, the spikes 66 and 70 engage and/or extend into the valvular wall 74 to inhibit axial movement of the prosthesis 50 relative to the valve wall 74.

Figures 5, 6A:
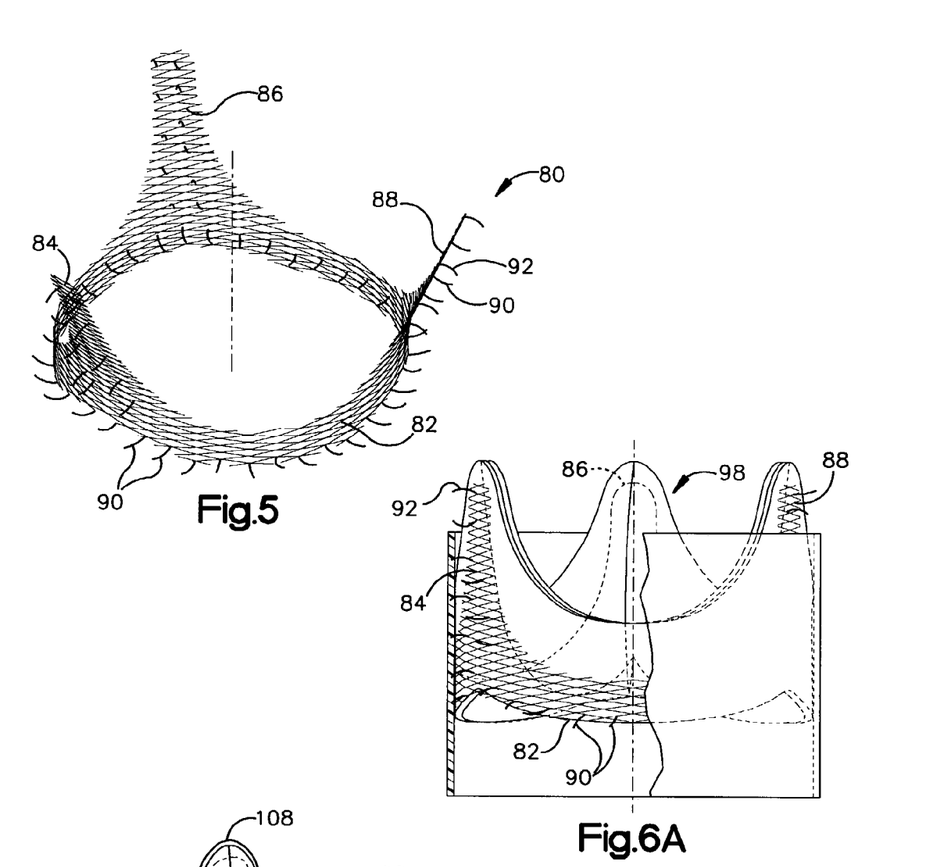
FIG. 5 is another example of a stent apparatus in accordance with the present invention.
FIG. 6A is an example of the stent of FIG. 5 mounted within an enclosure in accordance with the present invention.

FIG. 5 illustrates another example of a stent apparatus 80 which may be utilized as part of a valvular prosthesis in accordance with an aspect of the present invention. The stent 80 includes a generally annular base portion 82 and a plurality of axially extending portions (or stent posts) 84, 86 and 88 extending generally axially from the base portion. The post portions 84, 86 and 88 are circumferentially spaced apart for generally radial alignment with corresponding commissure posts of an associated valve wall. While the example of the stent 80 in FIG. 5 has three stent posts 84, 86 and 88, those skilled in the art will understand and appreciate that other numbers of posts also could be utilized in accordance with an aspect of the present invention. Typically, however, the number of posts and their relative circumferential position correspond to the number of leaflets of a valve to be mounted within the stent 80.

In accordance with an aspect of the present invention, each of the stent posts 84, 86, 88 may extend radially outwardly an angle Θ relative to the axis A. By way of example, the angle Θ may range from about 10 to about 60 degrees relative to a line drawn through the juncture of each post and the base 82 parallel to the central axis A. The outwardly extending posts 84, 86, and 88 facilitate engagement between each respective post and surrounding tissue when implanted, as the posts (being resilient) tend to urge radially outwardly and into engagement with such tissue.

The stent 80 also includes a plurality of spikes 90 and 92 that extend radially outwardly from the stent. In particular, some outwardly extending spikes 90 are curved generally toward an outflow end of the stent and others 92 are curved generally toward an inflow end of the stent. In addition, a row of spikes 90 may extend outwardly relative to the stent 80 at the inflow end thereof, which spikes also are curved generally toward the outflow end. The varying contour of the spikes 90 and 92 mitigates axial movement of the stent 80 (in both axial directions) relative to tissue engaged thereby, such as after being implanted. It is to be understood and appreciated that, while a single row of spikes is illustrated near the inflow end of the stent in FIG. 5, two or more axially spaced apart rows of spikes extending generally radially outwardly from the stent 80 could also be utilized in accordance with an aspect of the present invention. The rows of spikes may be curved toward each other to provide a clamping function on surrounding tissue when implanted.

FIG. 6A illustrates the stent of FIG. 5 mounted within a tubular structure 94 that has an inner diameter that is substantially commensurate with the outer diameter of the base portion 82 of the stent 80. The tubular structure 94 may be formed of a plastic or other material effective to hold the stent posts 84, 86, and 88 at a radial inward position. In this way, the tubular structure 94 urges the stent posts 84, 86, and 88 radially inward to a position that facilitates mounting a valve 98 therein. For example, the valve 98 may be positioned within and connected to the stent 80, such as by sutures applied along the base portion 82 and the stent posts 84, 86, and 88; without having to manually hold each of the posts against corresponding parts of the valve.

Figure 6B:
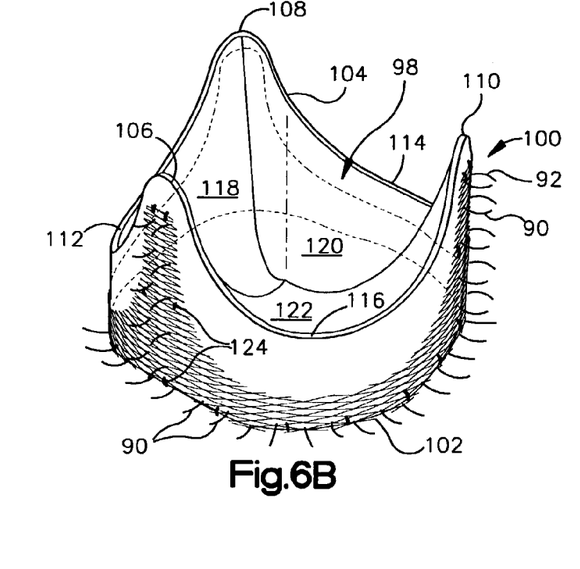
FIG. 6B is an example of valvular prostheses having the stent of FIG. 5 mounted therein in accordance with the present invention.

FIG. 6B illustrates an example in which a valve 98 has been mounted within the stent 80 of FIG. 5 to form a valvular prosthesis 100. The valve 98 includes an inflow end 102 and an outflow end 104. The inflow end 102 of the valve 98 is positioned adjacent relative to the inflow end of the stent 80. The outflow end 104 of the valve 98 is contoured to include axially extending commissure posts 106, 108 and 110 with sinuses 112, 114 and 116 located between each adjacent pair of posts. Valve leaflets 118, 120 and 122 extend between adjacent posts commensurate with the location of each of the sinuses 112, 114 and 116. The stent 80 may be connected to the valve 98 via sutures 124.

In accordance with an aspect of the present invention, the prosthesis 100 of FIG. 6B is a stented valve, which may be covered with an outer sheath of a substantially biocompatible material.

Figures 7, 8, 9A:
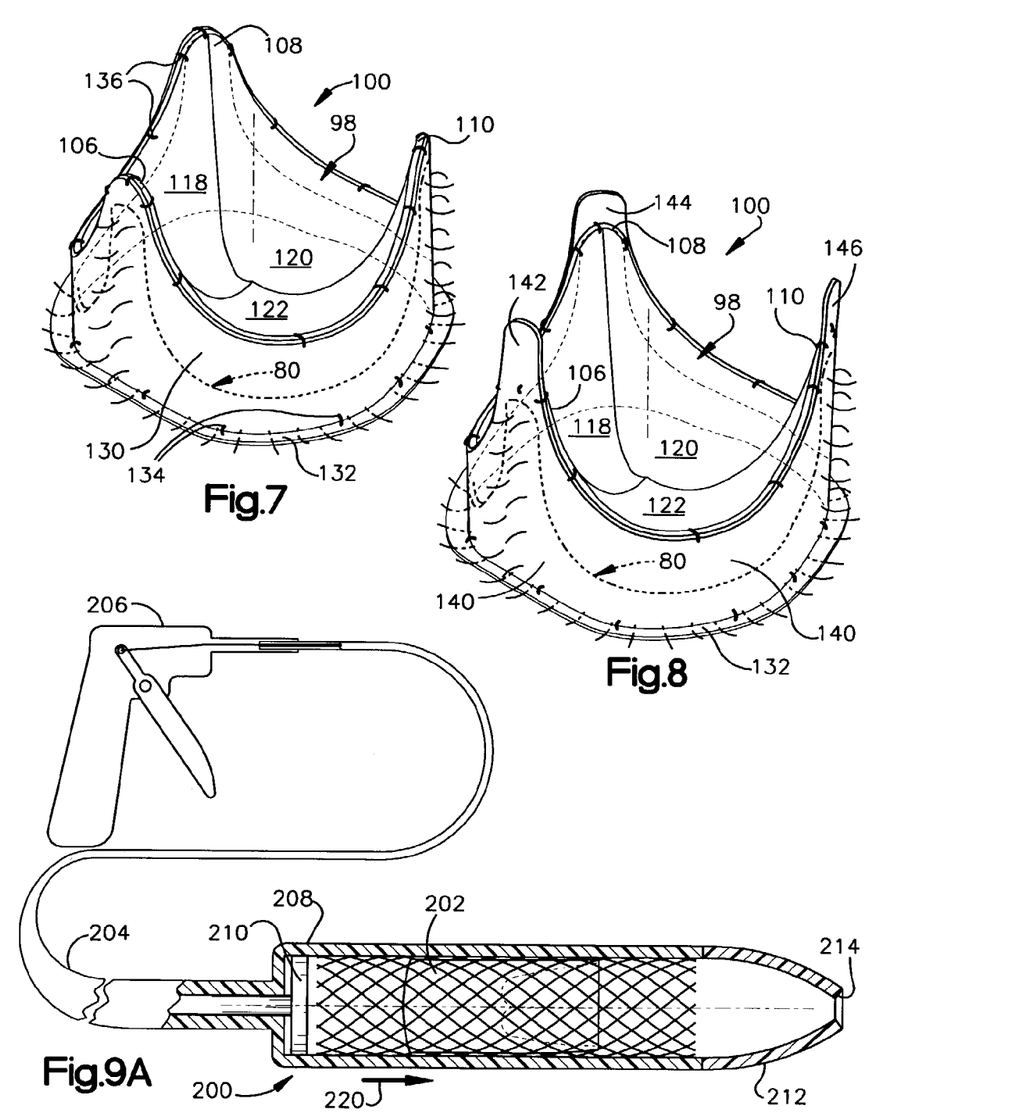
FIG. 7 is an example of a valvular prosthesis, illustrating an outer sheath over the prosthesis of FIG. 6B in accordance with the present invention.
FIG. 8 another example of a valvular prosthesis, illustrating an outer sheath over the prosthesis of FIG. 6B in accordance with the present invention.
FIG. 9A is an example of enclosure that may be utilized for implanting a valvular prosthesis in accordance with the present invention.

FIG. 7 illustrates an example of a valvular prosthesis in which an outer sheath 130 has been applied over the stent 80 and at least part of the exposed exterior portion of the valve 98 in accordance with an aspect of the present invention. As illustrated, the outer sheath 130 may have inflow and outflow ends having generally the same contour as the sidewall of the valve 98 and the stent 80. The outer sheath 130 may be a sheath of natural tissue pericardium (e.g., bovine, equine, porcine, etc.), another biological tissue material (e.g., collagen), or a synthetic material (e.g., Dacron). When a biological tissue is utilized, for example, it may be cross-linked with glutaraldehyde and detoxified with heparin bonding, such as one of the NO-REACT® natural tissue products that are commercially available from Shelhigh, Inc. of Millburn, N.J.

An implantation flange (or sewing ring) 132 may be formed at the inflow end of the prosthesis 100. The implantation flange 132 may be formed of substantially the same material as the outer sheath 140, such as formed from the outer sheath 130 or by attaching a separate flange by other methods. The outer sheath 130 may be attached to the valve 98 and/or to the stent 80 by applying sutures 134 and 136 at the respective inflow and outflow ends of the prosthesis 100. Some of the spikes 90, 92 may extend through the outer sheath 130 so as to mitigate axial movement of the prosthesis 100 relative to surrounding tissue when the prosthesis is implanted. Sutures 134 and 136 may be applied respectively at the inflow and outflow ends to secure the outer sheath relative to the stent 80 and the valve 100. The outer sheath 130 may include an outflow end that conforms to the contour of the outflow end 104 of the valve 100.

FIG. 8 illustrates another example of valvular prosthesis 100 that is similar to that shown and described in FIG. 7, in which identical reference numbers refer to corresponding parts previously identified herein. The prosthesis 100 includes having an outer sheath 140 that is disposed about the stent 80 and the valve 98 and having an outflow end that follows the contour of the prosthesis 100 (e.g., generally sinusoidal. In addition, the outer sheath 140 includes a plurality of axially extending lobes 142, 144 and 146 extending axially beyond the outflow attachment of the valve leaflets 118, 120, and 122. In this example, the lobes 142, 144 and 146 extend axially a length beyond the commissure posts 106, 108 and 110 of the valve 98. The axially extending lobes 142, 144 and 146 provide additional structure that may be utilized to help secure the prosthesis 100 relative to surrounding tissue when being implanted. When the prosthesis 100 of FIG. 8 is implanted, for example, sutures may be applied through the lobes 142, 144 and 146 to help secure the commissure posts of the prosthesis relative to the surrounding tissue. Additional sutures also could be applied at the inflow end to the implantation flange 132 located thereat.

Figure 9B:
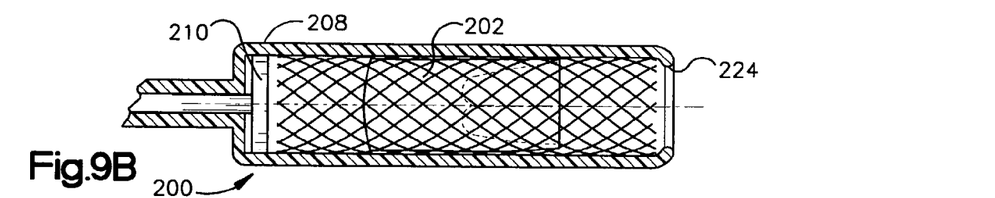
FIG. 9B is an example of another enclosure catheter mechanism that may be utilized for implanting a valvular prosthesis in accordance with the present invention.

FIGS. 9A and 9B illustrate variations of an implantation apparatus 200 that may be utilized to implant a valvular prosthesis 202 in accordance with an aspect of the present invention. It is to be understood and appreciated that any of the prosthesis shown and/or described herein may be implanted with such an implantation apparatus.

With reference to FIG. 9A, by way of example, the implantation apparatus 200 may be in the form of a catheter system. The implantation apparatus includes an elongated connecting element 204 extending between a trigger mechanism 206 and an enclosure 208, in which the prosthesis 202 is located. At least a portion of the prosthesis 202 is located within the enclosure 208. A plunger mechanism 210 is located at a proximal end of the enclosure 208 for urging the prosthesis 202 generally axially from the enclosure 208. An opposite end 212 of the enclosure 208 may be formed of a pliable material or a plurality of moveable members that may open as the prosthesis 202 is urged through an opening 214 located at a distal end. It is to be appreciated that the length of the connecting element 204 may vary according to where the valvular prosthesis 202 is to be implanted and the method of implantation.

The valvular prosthesis 202 is illustrated within the enclosure 208 in a compressed condition, such as described above. That is, the valvular prosthesis 202 within the enclosure 208 has a cross-sectional dimension that is less than its normal cross-sectional dimension, being maintained in such position by the enclosure. Those skilled in the art will appreciate that the orientation of the valvular prosthesis 202 will vary depending upon the direction in which blood is to flow through the valve when implanted.

By way of example, the external stent of the valvular prosthesis 202 may be formed of a deformable material, such as a shape memory alloy material (e.g., nitinol), which maintains its shape when cooled. Accordingly, the prosthesis 202 may be cooled (e.g., within a suitable fluid), compressed to a desired reduced cross-sectional dimension so as to fit within the enclosure 208, and then inserted within the enclosure. The prosthesis 202, after the stent being heated (e.g. to an ambient temperature), may desire to expand to its original dimension and configuration. However, the enclosure 208 or another retaining mechanism, such as a suture or other tubular member around the prosthesis, may be used to restrict its expansion. The compression of the valvular prosthesis 202 may be performed just prior to surgery to mitigate undesired permanent deformation of the valvular prosthesis 202. The plunger mechanism may be urged in the direction of arrow 220, such as by activating the trigger 206. Movement of the plunger 210, in turn, causes the prosthesis 202 to also be moved in the direction of the arrow 220. As the prosthesis 202 is urged through the opening 214 and discharged therefrom, the prosthesis may expand. Accordingly, the opening 214 should be positioned at the location where the prosthesis 202 is to be implanted prior to discharge. When the prosthesis 202 expands toward its original condition, the sidewall of the stent and/or spikes associated with the stent may engage and/or be urged into surrounding tissue so as to mitigate axial movement of the prosthesis relative to the surrounding tissue. As a result, the prosthesis may be implanted without sutures to provide an operable valve, such as a heart valve or a venous valve. When a valvular prosthesis is being employed as a heart valve, in accordance with present invention, it will be appreciated that the prosthesis may be implanted either as part of an open chest procedure or the patient's chest may be closed. Additionally, other expandable stent structures also could be utilized in accordance with an aspect of the present invention.

FIG. 9B illustrates another example of an enclosure 208 which may be utilized, in accordance with an aspect of the present invention, to implant a prosthesis 202. The enclosure 208 has an opening 224 at its distal end through which the prosthesis 202 may be discharged. In this example, the opening 224 is about the same diameter as the enclosure itself, although it may be curved slightly inwardly at the distal end thereof. This facilitates discharge of the prosthesis 202 without having an expandable distal end portion, such as shown and described with respect to FIG. 9A.

Figure 10:
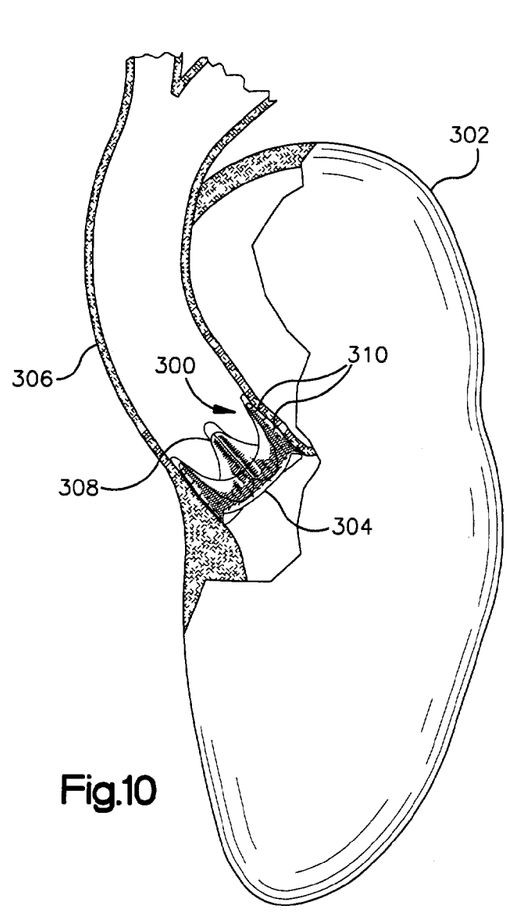
FIG. 10 is an example of a valvular prostheses implanted in an aortic position of a heart in accordance with the present invention.

FIG. 10 illustrates an example of a valvular prosthesis 300 implanted in a heart 302 in an aortic position. When being implanted at an aortic position, an aortic valve (e.g., equine, porcine, bovine, etc.) may be utilized for the valve portion of the prosthesis, although other types of valve portion also could be used. Prior to implanting the prosthesis 300, the aortic valve or at least calcified portions thereof should be removed. An inflow end 304 of the prosthesis 300 is annularized with respect to the annulus of the aorta 306. An outflow portion 308 of the prosthesis 300 extends axially into the aorta 306, with the stent posts engaging the interior of the aortic wall. As mentioned above, a plurality of spikes 310 may extend laterally from the stent portion of the valvular prosthesis 300 to engage the aorta 306 to help maintain a desired axial orientation of the valvular prosthesis relative to the aorta 306.

The valvular prosthesis 300 may be implanted in a compressed condition. It is to be appreciated that the valvular prosthesis 300 may be implanted in the aortic position during a conventional open chest procedure or during a closed chest procedure. The valvular prosthesis 300 may be implanted by using a catheter (or other structure) to retain the prosthesis in a compressed condition. The catheter may then be used to position the valve at a desired position, such as by utilizing a suitable imaging technology (e.g., x-ray, ultrasound, or other tomography device) or a direct line of sight. Once at the desired position, the prosthesis 300 may be discharged from its retaining mechanism (e.g., an enclosure) so that it expands toward its original expanded configuration at the desired position within the aorta 306.

It is to be understood and appreciated, though, if the patient has a calcified aortic valve, the patient typically must be put on cardiopulmonary bypass to remove the calcium and implant the valve. Advantageously, a valvular prosthesis 300 in accordance with the present invention may be implanted more efficiently so as to mitigate morbidity and mortality of the patient. In addition, the prosthesis may be implanted without sutures or, alternatively, some sutures may be utilized. For example, sutures may be applied at the inflow end 304 (e.g., at a sewing ring) and/or at the outflow end 308, such as when the prosthesis is configured to have axially extending lobes (see FIG. 8).

Figure 11:
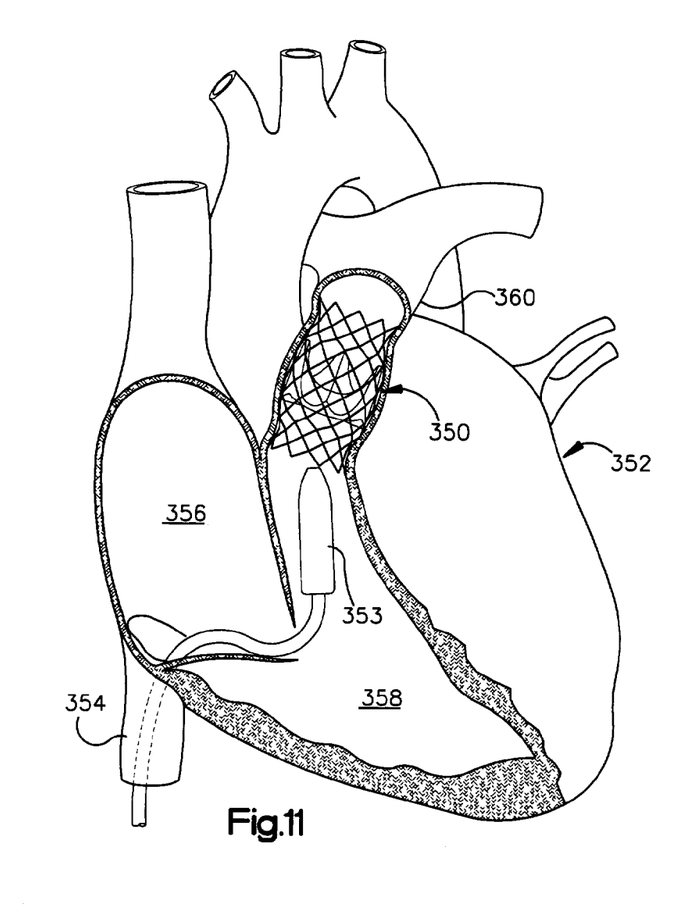
FIG. 11 is an example of a valvular prostheses implanted in a pulmonic position of a heart in accordance with the present invention.

FIG. 11 illustrates an example of a valvular prosthesis 350 implanted in a pulmonary position of a heart 352. The particular example illustrated in FIG. 11 shows an enclosure 353, such as may be part of a catheter, which has been inserted into the heart 352 to place the prosthesis at a desired position. Specifically, the catheter has traveled through the inferior vena cava 354, into the right atrium 356 and into the right ventricle 358 to position the valvular prosthesis 350 at a desired position relative to the pulmonary artery 360.

As mentioned above, the prosthesis 350 is mounted within the enclosure 353 in a compressed condition prior to implantation. The enclosure 353 and the prosthesis 350, for example, may be introduced into the inferior vena cava through the patient's right femoral vein. The prosthesis 350 and enclosure 353 may traverse the vascular system to the inferior vena cava 354 with the assistance of suitable imaging equipment such as x-ray, ultrasound, or other imaging devices. The imaging equipment is utilized to navigate the enclosure 353 and the prosthesis 350 to the desired position. Once at the desired position, such as at the opening to the pulmonary artery 360, the prosthesis 350 may be discharged through a distal opening of the enclosure 353. The valvular prosthesis 350 then expands from its compressed condition to an expanded condition, as illustrated in FIG. 11. Advantageously, when the valvular prosthesis 350, which is formed of an elastic material (e.g., nitinol in its heated form), is urged through the opening of the enclosure 353, it will automatically expand and dilate, thereby also expanding the valve that is attached to the stent. Therefore, the valvular prosthesis 350 becomes functional almost immediately. The enclosure 353 may then removed out of the heart 352, through the inferior vena cava 354 and removed from the patient.

Advantageously, the valvular prosthesis 350 may be implanted in the patient without cardiopulmonary bypass. As a result, a significant amount of time may be saved with less stress on the patient, thereby mitigating the risks of morbidity and mortality associated with conventional open-heart surgery typically employed to implant a heart valve prosthesis. Those skilled in the art will understand and appreciate that this process also may be utilized to implant a valvular prosthesis for a venous valve, such as in a patient's lower limb.

What has been described above includes examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims. Furthermore, to the extent that the term "includes" and variants thereof or the term "having" and variants thereof are used in either the detailed description or the claims, each such term is intended to be inclusive in a manner similar to the term "comprising."

What is claimed is:

1. A valvular prosthesis comprising:
   a stent apparatus;
   a valve apparatus located within a stent apparatus to define a stented valve, the valve apparatus having inflow end and a generally sinusoidal outflow end, the inflow and outflow ends being spaced apart from each other by a length of a sidewall portion, the valve apparatus comprising an animal pulmonic heart valve that includes a plurality of leaflets attached to and extending from an interior part of the sidewall portion located within the stent apparatus, wherein each of the valve apparatus and the stent apparatus has a generally sinusoidal outflow end comprising axially extending posts with sinuses between adjacent posts, such that the plurality of stent posts are aligned substantially radially with and attached to corresponding posts of the valve apparatus;
   the stented valve being deformable between a reduced cross-sectional dimension and an expanded cross-sectional dimension, whereby placement of the stented valve to a desired implantation position is facilitated when in the reduced cross-sectional dimension; and
   the stent apparatus being self-expanding to urge the stented valve from the reduced cross-sectional dimension toward the expanded cross-sectional dimension thereof, whereby implantation is facilitated and the leaflets are movable between open and closed conditions to provide for substantially unidirectional flow of blood through the stented valve when in the expanded cross-sectional dimension thereof; and
   an outer sheath of a substantially biocompatible material that covers at least a substantial portion of the stent apparatus and the valve apparatus.

2. The prosthesis of claim 1, the stent apparatus further comprising an annular base portion at an inflow end thereof, a plurality of spikes extending generally radially outwardly from the stent apparatus, at least a substantial portion of the plurality of spikes extending through the outer sheath, whereby, when the stented valve is implanted within tissue, at least some of the spikes engage the tissue to inhibit movement of the stented valve relative to the tissue.

3. A valvular prosthesis comprising:
a stent apparatus;
a valve apparatus located within a stent apparatus to define a stented valve, the valve apparatus having inflow end and a generally sinusoidal outflow end, the inflow and outflow ends being spaced apart from each other by a length of a sidewall portion, the valve apparatus comprising an animal pulmonic heart valve that includes a plurality of leaflets attached to and extending from an interior part of the sidewall portion located within the stent apparatus;
the stented valve being deformable between a reduced cross-sectional dimension and an expanded cross-sectional dimension, whereby placement of the stented valve to a desired implantation position is facilitated when in the reduced cross-sectional dimension; and
the stent apparatus being self-expanding to urge the stented valve from the reduced cross-sectional dimension toward the expanded cross-sectional dimension thereof, whereby implantation is facilitated and the leaflets are movable between open and closed conditions to provide for substantially unidirectional flow of blood through the stented valve when in the expanded cross-sectional dimension thereof; and
a sheath of a substantially biocompatible biological material covering the stent apparatus and at least a portion of the valve, the stent apparatus further comprising a plurality of spikes extending generally radially outwardly from the stent apparatus, at least a substantial portion of the plurality of spikes extending through the outer sheath, at least some of the spikes extending through the sheath whereby, when the stented valve is implanted within tissue, at least some of the spikes engage the tissue to inhibit movement of the stented valve relative to the tissue.

4. A valvular prosthesis comprising:
a stent apparatus comprising a plurality of stent posts extending generally axially from a stent base portion to define a substantially sinusoidal outflow end of the stent apparatus that includes a; plurality of leaflets attached to and extending from an interior part of a sidewall
a pulmonic animal heart valve located within a stent apparatus, the heart valve having an inflow end and a generally sinusoidal outflow end with posts and sinuses that are aligned substantially radially with corresponding posts and sinuses of the stent apparatus with the inflow and; outflow ends being spaced apart from each other by a length of the side wall
an outer sheath of a substantially biocompatible biological material that covers at least a substantial portion of the stent apparatus and the valve apparatus to define a stented valve;
the stented valve being deformable between a reduced cross-sectional dimension and an expanded cross-sectional dimension, whereby placement of the stented valve to a desired implantation position is facilitated when in the reduced cross-sectional dimension; and
the stent apparatus being self-expanding to urge the stented valve from the reduced cross-sectional dimension toward the expanded cross-sectional dimension thereof, whereby implantation is facilitated and the leaflets are movable between open and closed conditions to provide for substantially unidirectional flow of blood through the stented valve when in the expanded cross-sectional dimension thereof.

5. The prosthesis of claim 4, wherein an outflow end portion of the outer sheath defines a plurality of lobes that extend beyond the outflow end of the stented valve at respective posts of the valve apparatus.

6. The prosthesis of claim 4, wherein the stent apparatus further comprises an annular base portion at an inflow end thereof, a plurality of spikes extending generally radially outwardly from the stent apparatus, at least a substantial portion of the plurality of spikes extending through the outer sheath, whereby, when the stented valve is implanted within tissue, at least some of the spikes engage the tissue to inhibit movement of the stented valve relative to the tissue.

* * * * *

UNITED STATES PATENT AND TRADEMARK OFFICE
CERTIFICATE OF CORRECTION

| | | |
|---|---|---|
| PATENT NO. | : 7,025,780 B2 | Page 1 of 1 |
| APPLICATION NO. | : 10/373138 | |
| DATED | : April 11, 2006 | |
| INVENTOR(S) | : Shlomo Gabbay | |

It is certified that error appears in the above-identified patent and that said Letters Patent is hereby corrected as shown below:

Column 12, lines 1-3, after "apparatus" delete "that includes a; plurality of leaflets attached to and extending from an interior part of a sidewall"

Column 12, line 5, after "apparatus" insert --that includes a; plurality of leaflets attached to and extending from an interior part of a sidewall--

Signed and Sealed this

Tenth Day of April, 2007

JON W. DUDAS
*Director of the United States Patent and Trademark Office*